United States Patent
Altman et al.

(10) Patent No.: US 12,364,876 B2
(45) Date of Patent: Jul. 22, 2025

(54) DEVICE AND METHOD FOR TREATING DRY EYES

(71) Applicant: LUMENIS BE LTD, Yokneam (IL)

(72) Inventors: Hernan Altman, Kyriat Tivon (IL); Joseph Birman, Haifa (IL)

(73) Assignee: LUMENIS BE LTD. (IL)

( * ) Notice: Subject to any disclaimer, the term of this patent is extended or adjusted under 35 U.S.C. 154(b) by 770 days.

(21) Appl. No.: 17/565,747

(22) Filed: Dec. 30, 2021

(65) Prior Publication Data

US 2022/0118281 A1 Apr. 21, 2022

Related U.S. Application Data (63) Continuation-in-part of application No. 16/367,774, filed on Mar. 28, 2019, now Pat. No. 11,285,334.

(60) Provisional application No. 63/131,856, filed on Dec. 30, 2020.

(51) Int. Cl.
*A61N 5/06* (2006.01)

(52) U.S. Cl.
CPC ......... *A61N 5/0625* (2013.01); *A61N 5/0624* (2013.01); *A61N 2005/063* (2013.01); *A61N 2005/0648* (2013.01)

(58) Field of Classification Search
CPC ............ A61N 1/40; A61N 5/0613; A61N 2005/0651; A61N 2005/0644
See application file for complete search history.

(56) References Cited

U.S. PATENT DOCUMENTS

| | | | |
|---|---|---|---|
| 6,454,763 B1* | 9/2002 | Motter | A61F 9/00802 606/15 |
| 2006/0167531 A1* | 7/2006 | Gertner | A61N 5/0603 607/86 |
| 2013/0172959 A1* | 7/2013 | Azoulay | A61F 9/008 607/90 |
| 2015/0025604 A1 | 1/2015 | McClellan | |
| 2019/0299016 A1 | 10/2019 | Altman | |

FOREIGN PATENT DOCUMENTS

| | | |
|---|---|---|
| JP | S6019814 | 10/1985 |
| JP | 2019072365 | 5/2019 |
| KR | 20170122323 | 11/2017 |

OTHER PUBLICATIONS

Search Report—Corresponding PCT Application No. PCT/IB2021/062485, dated May 11, 2022, 3 pages.

* cited by examiner

*Primary Examiner* — Rex R Holmes
(74) *Attorney, Agent, or Firm* — ISUS INTELLECTUAL PROPERTY PLLC; Anthony Jason Mirabito (57) ABSTRACT

The present disclosure discloses a device for treating eyelids or other body regions of a subject. The device includes a fiber bundle having a distal end and a proximal end. The proximal end is connectable to an optical coupler designed for optical coupling with a light source. The device further includes a rigid tube, housing at least a portion of the distal end of the fiber bundle and a cover member mounted around a portion of the rigid tube. The cover member is rotatable relative to the rigid tube during treatment of the eyelids of the subject. The rotation of the cover member relative to the rigid tube allows the device to be operated in different orientations as may be required during the treatment of eyelids.

17 Claims, 9 Drawing Sheets

DEVICE AND METHOD FOR TREATING DRY EYES

RELATED APPLICATIONS

This application is a continuation to U.S. Provisional Application No. 63/131,856, filed Dec. 30, 2020, entitled "Device and Method for Treating Dry Eyes", and is a Continuation-In-Part to U.S. patent application Ser. No. 16/367,774, filed Mar. 28, 2019, now U.S. Pat. No. 11,285,334, issued on Mar. 29, 2022, entitled "Apparatus and Method for Treatment of Dry Eyes", the entire contents of both of which are herein incorporated by reference and to which two applications priority is claimed.

TECHNICAL FIELD

The present invention relates to a medical device and a method for treating dry eyes.

BACKGROUND

One main reason for dry eyes is Blepharitis, a chronic inflammation of the eyelid margin. This is because if eyelid glands are chronically inflamed, they produce too little or even no secretions, which leads to an unstable tear film. The treatment of chronic Blepharitis is not trivial, as it is often caused by pathogens such as bacteria and skin mites (demodex).

It has been shown that, for example, treatment with IPL (Intense Pulsed Light) therapy has a long-lasting effect and bacteria and skin mites are successfully eliminated. IPL is a light pulse therapy that may be used to treat the inflammatory causes of dry eye, stimulate the eyelid glands, and accelerate healing. Other light sources, such as LED or laser light, may be used. The use of a light source is for the purpose of generating heat, and causing photo modulation, so as to heat up the area of a Meibomian Gland, so other sources of generating heat may be used.

U.S. Pat. Nos. 9,333,370 and 10,085,814, assigned to the assignee of the present invention, are directed to dry eye treatments using light, and are herein incorporated by reference in their entireties.

During treatment, several pulses of light may be delivered to patient's eyelids. Care should be taken to avoid direct light entry into a cornea, as well as exposure of eyelashes to the energy (to avoid hair loss). In addition, direct heating of a cornea and other ocular surfaces should be avoided.

In the treatment of MGD (Meibomian Gland Dysfunction, or evaporative Dry Eye), Meibomian gland expression (MGX) is also a therapeutic approach, in which the glands are squeezed, generally after being heated through the use of IPL energy, LED energy or other energy, to force the meibum secretion out. Typically, this is achieved by pressing the eyelid from the outside with a finger, against a q-tip placed between the eyelid and the sclera. Sometimes, dedicated pincers or paddles are used for MGX.

The existing devices for treating dry eyes are rigid while handling and may not be adjustable for example to alter device orientations that may be required during treatment.

Therefore, there exists a need for an improved device that overcomes one or more of the limitations mentioned above.

SUMMARY

In an embodiment, the present disclosure discloses a device for treating eyelids of a subject. The device includes a fiber bundle having a distal end and a proximal end. The proximal end is connectable to an optical coupler designed for optical coupling with a light source. The device further includes a rigid tube housing at least a portion of the distal end of the fiber bundle and a cover member mounted around a portion of the rigid tube. The cover member is rotatable relative to the rigid tube during treatment of the eyelids of the subject.

In another embodiment, the present disclosure discloses a system for performing treatment of eyelids of a subject. The system may include a console. The console may include power electronics which provide power to a light generating device such as an IPL or a LED device. The console may also include a laser source in the event that the laser is the source of light energy to perform the eyelid treatment. The device includes a fiber bundle having a distal end and a proximal end. The proximal end includes an optical coupler designed for optical coupling with a light source in the console if so equipped. The console itself may include a cavity into which the proximal end of the fiber bundle is inserted. Alternatively, the proximal end of the fiber bundle may be adapted to fit within a cavity in an IPL or other handpiece. Known IPL devices include removable glass, sapphire or other transparent members that contact the skin of the patient and are adapted to transmit light from the IPL source through the transparent member and onto the skin of the patient. These transparent members may be removable to accommodate different size transparent members. Once such transparent member is removed, a cavity is presented such that the proximal end of the fiber bundle may be inserted into the cavity through a suitable interface member. The device further includes a rigid tube housing at least a portion of the distal end of the fiber bundle and a cover member mounted around a portion of the rigid tube. The cover member is rotatable relative to the rigid tube during treatment of the eyelids of the subject In another embodiment, the present disclosure discloses a method for treating Blepharitis or Meibomian gland dysfunction. The method includes treating patient's eyelids with a device as described above and squeezing the patient's eyelids to conduct Meibomian gland expression (MGX).

BRIEF DESCRIPTION OF THE ACCOMPANYING DRAWINGS

The embodiments of the disclosure itself, as well as a preferred mode of use, further objectives, and advantages thereof, will best be understood by reference to the following detailed description of illustrative embodiments when read in conjunction with the accompanying drawings. One or more embodiments are now described, by way of example only, with reference to the accompanying drawings in which.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description that follows may be better understood. It should be appreciated by those skilled in the art that the conception and specific embodiments disclosed may be readily utilized as a basis for modifying or designing other structures for carrying out the same purposes of the present disclosure. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Figure 1:
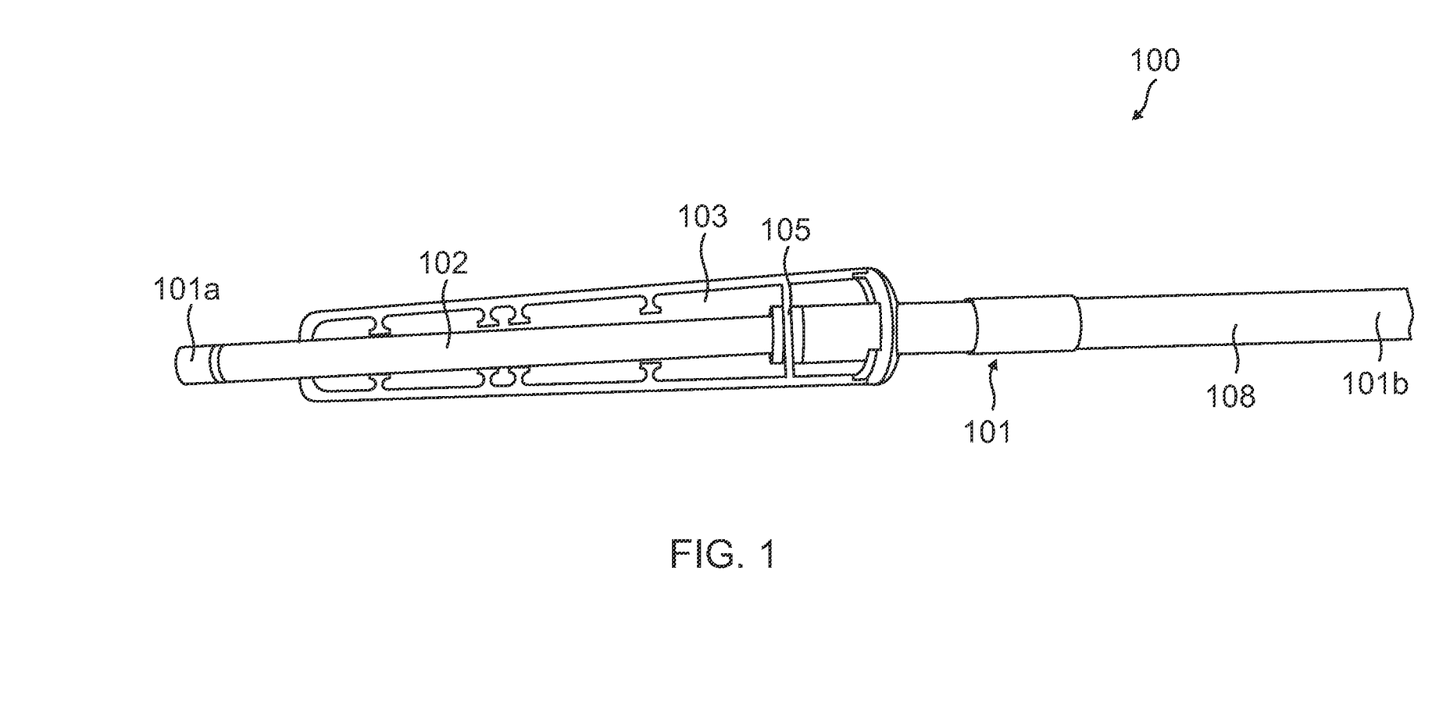
FIG. 1 shows a perspective, side view of a non-limiting example of a device for treating eyelids of a subject, in accordance with some embodiments of the present disclosure.

FIG. 1 shows a perspective, side view of a device (100) for treating eyelids of a subject. Here, eyelids of a subject may typically refer to eyelids of a human being, however the same should not be construed as a limitation of the present disclosure. The device (100) may be used to treat dry eye or MGD (Meibomian Gland Dysfunction). The device (100) as shown in FIG. 1 includes a fiber bundle (101) that has a distal end (101*a*) and a proximal end (101*b*). The fiber bundle (101) may be an optical fiber cable, also known as a fiber optic cable, in an assembly similar to an electrical cable but containing one or more optical fibers that are used to carry light for which light source may be an Intense Pulse Light (IPL) or another light source, such as LEDs. The fiber bundle (101) may also incorporate a filter to allow for wavelength selection as well as act as an energy damper to reduce the original fluence, emitted by the light source, to acceptable levels for eyelid treatment. In some embodiments and depending on the use case, the fiber bundle (101) may be disposable or reusable. A typical fiber bundle (101) may contain thousands of fibers with a plastic or silicon casing. The achieved treatment area is in a range of 5 mm-8 mm in diameter (assuming circular or semi-circular area).

Figure 8:
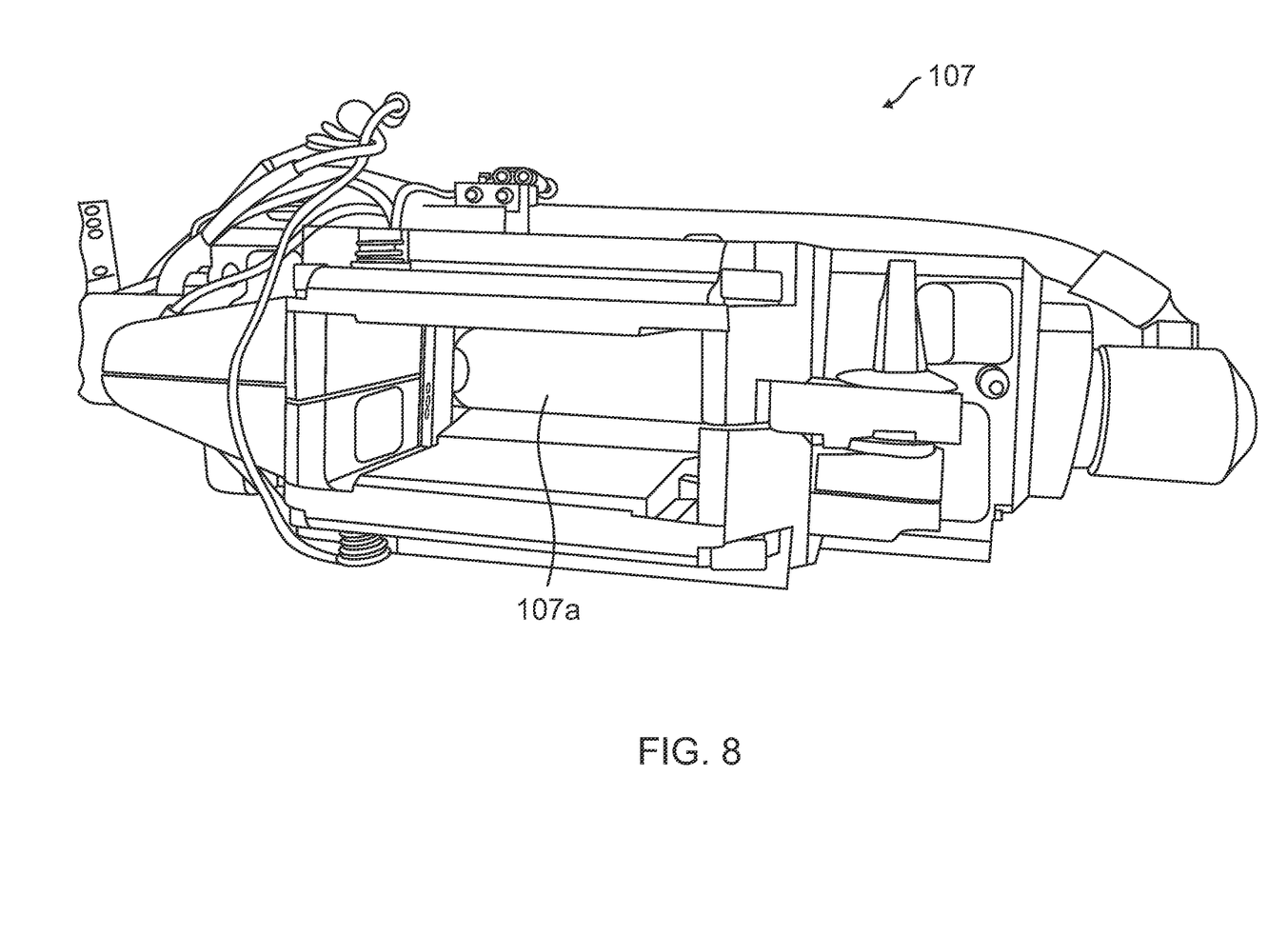
FIG. 8 shows a perspective view of an IPL device comprising a cavity to accommodate the connector of the device of FIG. 1 shown in FIGS. 7A and 7B, in accordance with some embodiments of the present disclosure.

In some embodiments, the proximal end (101*b*) of the fiber bundle (101) may be connectable to an IPL handpiece device [e.g., device 107 shown in FIG. 8], or to a main console having a similar socket which is configured to accept the proximal end (101*b*) of fiber bundle (101), as described above. Further, a portion of the fiber bundle (101) near the proximal end (101*b*) may be housed in a flexible member (108). The flexible member (108) may also be referred to as an umbilical cord. The fiber bundle (101) extending from the IPL device or any other console [not shown in the figure] may be housed within the flexible member (108) for a pre-defined distance. After that distance, and in general towards the distal end (101*a*) of the fiber, the fiber bundle (101) may be housed within a rigid tube (102). In some embodiments, the rigid tube (102) may be made of a metallic or plastic material. In some embodiments, the rigid tube (102) may be made of a composite material. The rigid tube (102) may be a hollow tubular member that receives a distal portion of the fiber bundle (101).

Further, as shown in FIG. 1, the device (100) includes a cover member (103) mounted around the rigid tube (102). In the figure, a cross section of the cover member is shown to allow illustrating the rigid tube (102) passing thereinside. In some embodiments, the cover member (103) may be mounted around the rigid tube (102) only and not around the flexible member (108). The cover member (103) may be used by an operator of the device (100) to hold and handle the device (100). The cover member (103) may be made of a polymeric material such as, but not limited to, plastic. The cover member (103) may be mounted around the rigid tube (102) such that it is freely rotatable relative to the rigid tube (102). This free rotation of the cover member (103) allows the operator to change the orientation of the device (100) during treatment as may be necessary and thus facilitates better treatment of dry eyes of a human being.

In some embodiments, the free, relative rotation of the cover member (103) about the rigid tube (102) may be facilitated by at least one bearing (105) mounted between the rigid tube (102) and the cover member (103). The bearing (105) may be provided as shown in FIG. 1 at a portion distal to the flexible member (108). However, position of the bearing (105) should not be construed as a limitation to the present disclosure, as it may be mounted anywhere along the path of intersection between the cover member (103) and the rigid tube (102). In some embodiments, the diameter of the rigid tube (102) may be higher until the point of provision of the bearing (105) and may then be reduced in diameter in the distal direction. In some embodiments, another metallic tube may be mounted around the rigid tube (102) up to the point of provision of the bearing (105).

Figure 2:
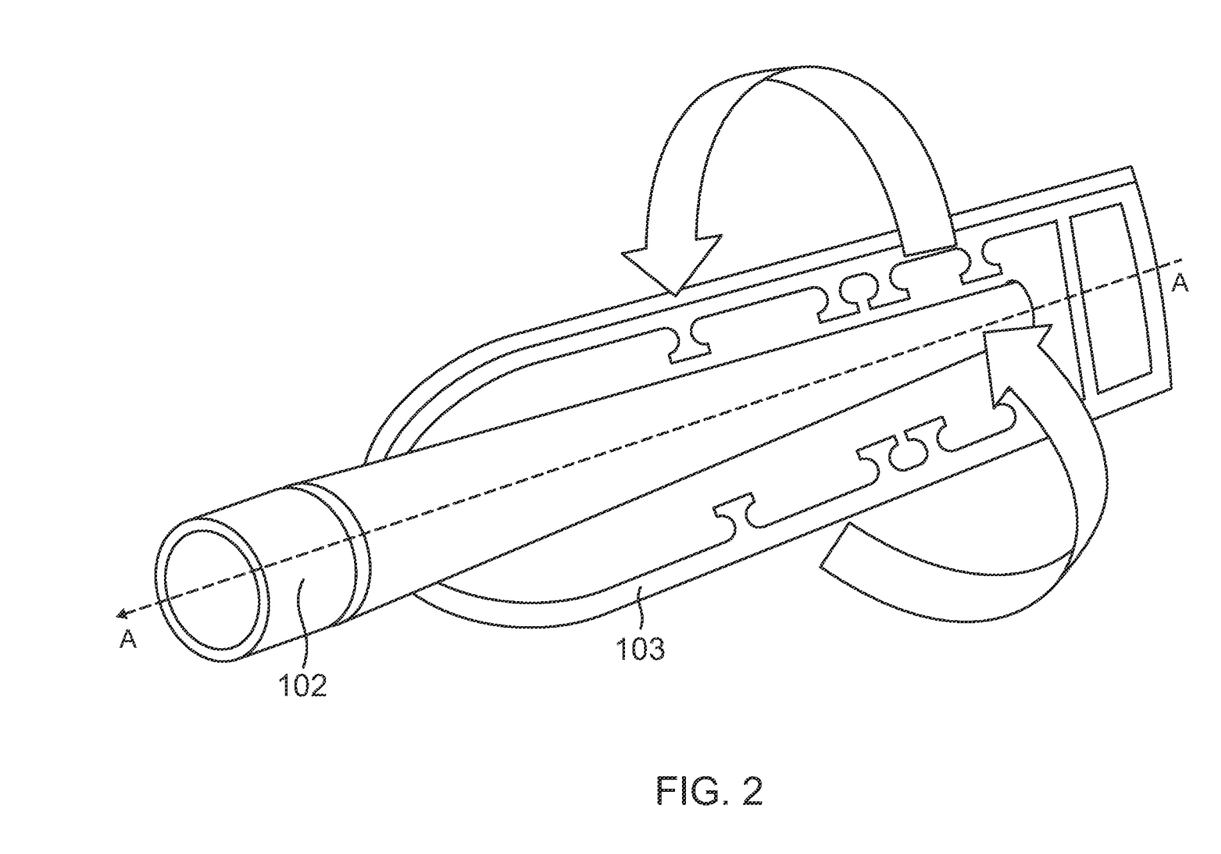
FIG. 2 shows a perspective view of the device of FIG. 1, showing rotation of a cover member with respect to a rigid tube, in accordance with some embodiments of the present disclosure.

Referring now to FIG. 2, this figure shows a perspective view of the device (100). As can be seen, the cover member (103) may be provided such that it is freely rotatable around rigid tube (102) about a longitudinal axis (A-A) of the rigid tube (102). During the rotation, the rigid tube (102), as the name suggests, is rigid, and only the cover member (103) may rotate about the longitudinal axis (A-A) to allow the operator to operate the device (100) at different orientations during the treatment. Since cover member (103) is freely rotatable around rigid tube (102), rotating cover member (103) will not rotate rigid tube (102) and will not generate torque forces on the rigid tube (102) or fiber bundle (101).

Figure 3:
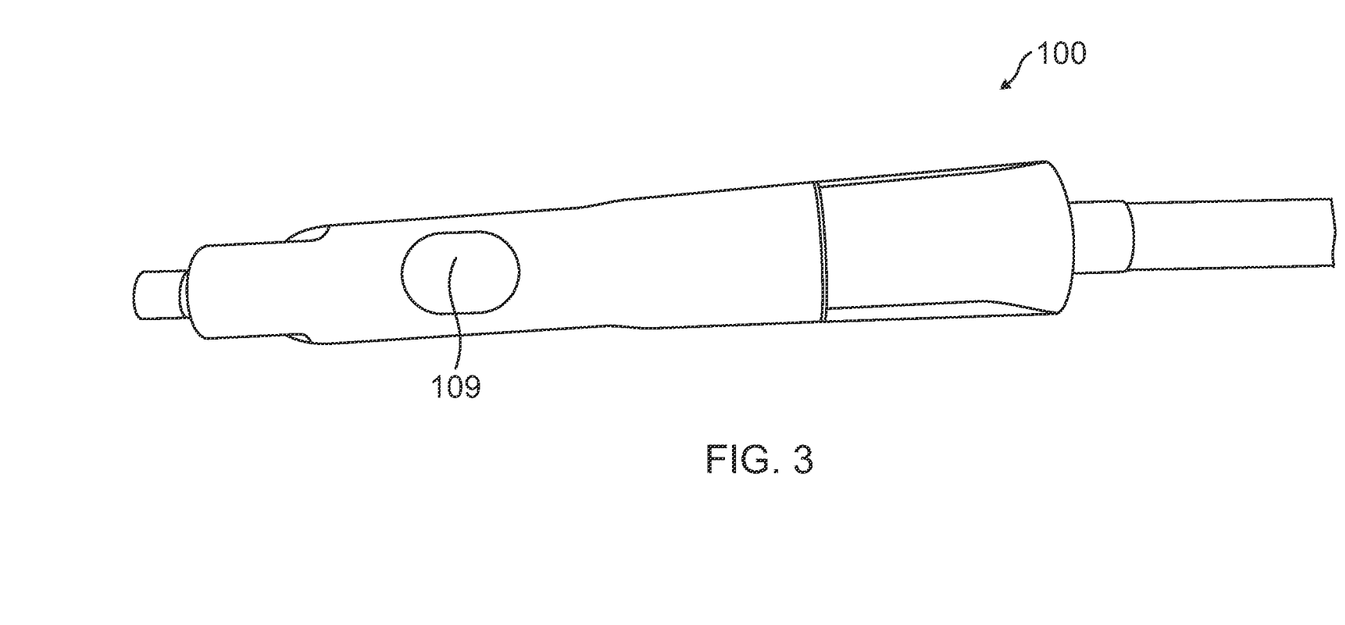
FIG. 3 shows a top perspective view of the device of FIG. 1 provided with a switch to activate the device, in accordance with some embodiments of the present disclosure.

FIG. 3 shows a switch (109), which may also be embodied as a trigger or push button, provided on the cover member (103) of the device (100). The switch (109) may be selectively operated to ON or OFF condition as may be necessary during the treatment. Switching ON the device (100) may cause light from the IPL or other source to pass through the fiber bundle (101) which is used for the treatment. In some embodiments, switch (109) may be permanently OFF and may be operated into an ON state by an operator.

Figure 4:
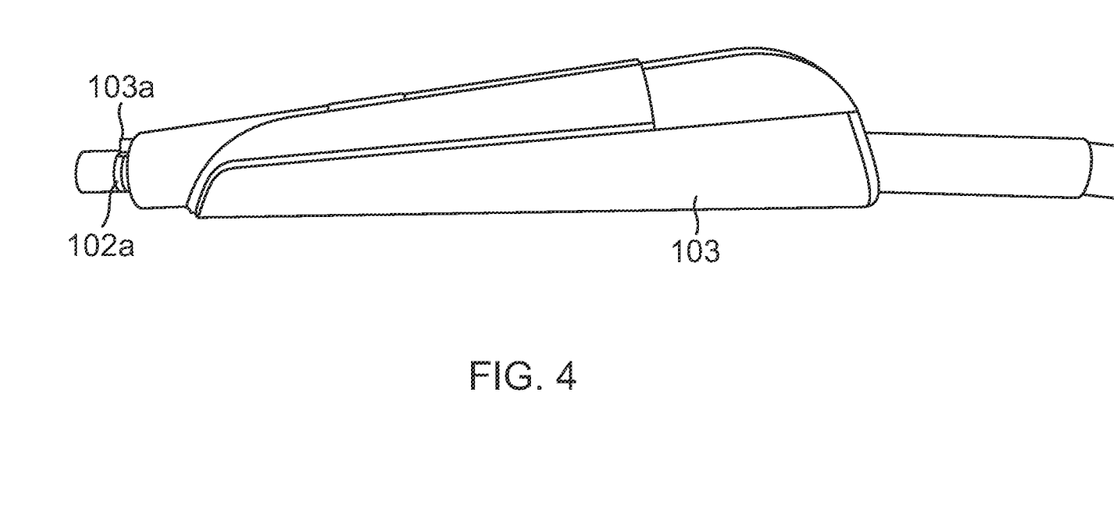
FIG. 4 shows a side view of the device of FIG. 1, in accordance with some embodiments of the present disclosure.
Figure 5:
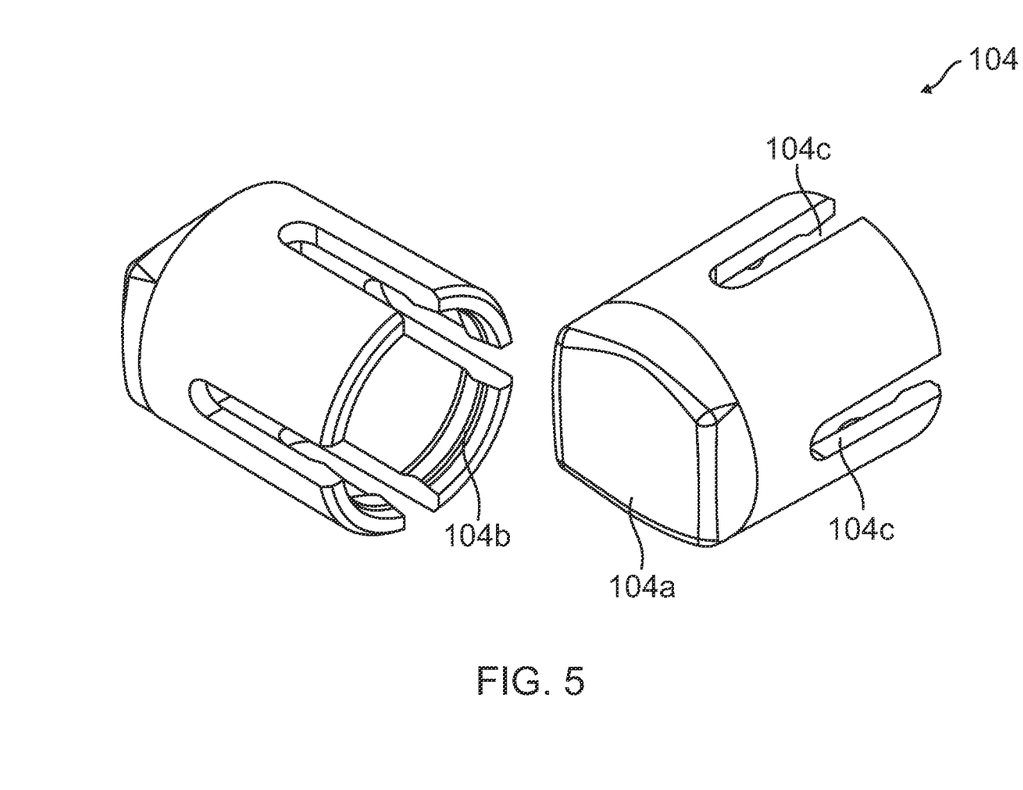
FIG. 5 shows perspective views of a disposable plug connectable to the rigid tube of the device of FIG. 1, in accordance with some embodiments of the present disclosure.

FIG. 4 shows a side view of the device (100). As shown, the cover member (103) is defined with a distal projection (103a) that facilitates connection of the cover member (103) with a removable/disposable tip (104) that is shown in FIG. 5. In some embodiments, there may be more than one projection (103a) that allows connection between the cover member (103) and the disposable tip (104). In some embodiments, the disposable tip (104) may be defined with one or more projections and the cover member (103) may be defined with notches to allow assembly of the disposable tip (104) and the cover member (103) and hence, method of assembly should not be construed as a limitation of the present disclosure. Further, the rigid tube (102) may be defined with a slit (102a) that allows placement of the disposable tip (104) on the rigid tube (102). The slit (102a) may be circumferential extending around the rigid tube (102). In some embodiments, the disposable tip (104) may be defined with the slit to allow placement of the disposable tip (104) over the rigid tube (102).

Referring now to FIG. 5, which shows front and rear perspective views of the disposable tip (104) that may be used for treatment of eyelids of the subject. The disposable or removable tip (104) may be constructed of a bio-compatible, transparent or translucent material, such as silicone or polycarbonate, which allows delivery of light energy to an eyelid. The disposable tip (104) may be provided in clean/sterile state or packaging, for example one for patient or for each eye, to allow hygienic treatment for every patient. During the procedure, the disposable tip's packaging may be opened and the disposable tip (104) may be mounted over the distal end (101a) of the fiber bundle (101). Mounting may be accomplished by use of an adhesive, or force-fitted (friction between sides of the fiber bundle (101) and an annular part of the disposable tip (104) surrounding the fiber bundle (101)), snap on and off, or form-fitted (e.g., by a thread).

During the treatment, the light beam may be transmitted via the fiber bundle (101) from the proximal end (101b) to the distal end (101a) of the fiber bundle (101) and then into the disposable tip (104). The disposable tip (104) transmits the light beam via a contact surface (104a) to the patient's eyelid. A rounded, solid or soft tip, allows a comfortable interface for the physical contact between the disposable tip (104) and the eyelid. The contact surface (104a) of the disposable tip (104) may also be curved so that, when contacting the eyelid, the softness of the material distributes the force and the pressure on the eyelid. In some embodiments, the contact surface (104a) of the disposable tip (104) may have a concave shape which enables better conformation to the natural curvature of the eyelid.

The disposable tip (104), as shown in FIG. 5, may be defined with a plurality of notches (104c). As an example, there may be four notches (104c) defined around circumference of the disposable tip (104). One of these notches (104c) may be aligned with the projection (103a) in of the cover member (103) to facilitate connection of the disposable tip (104) with the cover member (103). Since the cover member (103) and the disposable tip (104) are assembled with each other, any rotation of the cover member (103) about the longitudinal axis (A-A) of the rigid tube (102) will also lead to rotation of the disposable tip (104). Thus, the cover member (103) along with the disposable tip (104) may rotate about the longitudinal axis (A-A) of the rigid tube (102). As mentioned above, this joint rotation of disposable tip (104) and cover member (103) will not rotate rigid tube (102) or fiber bundle (101) or create any torque forces on them.

Advantageously, the free rotation of the disposable tip (104) with the cover member (103) allows the device (100) to be operated in different orientations during the treatment of the eyelid and thus the contact surface (104a) of the disposable tip (104) may contact the eyelid as desired and appropriate for the treatment. For example, if a vertical portion of the contact surface (104a) of the disposable tip (104) is to be placed in contact with the eyelid during the treatment, the operator can make a simple adjustment of rotation of the cover member (103) along with the disposable tip (104) so as to achieve the required contact with the eyelid. The operator may decide the orientation based on factors such as, but not limited to, area of contact required between the contact surface (104a) of the disposable tip (104) and the eyelid.

Further, as shown in FIG. 5, the disposable tip (104) may be defined with a bulge (104b) at its inner surface. The bulge (104b) allows the placement of the disposable tip (104) on the rigid tube (102) at the distal end (101a) of the fiber bundle (101). The bulge (104b) may be placed on the slit (102a) defined on the rigid tube (102) for connection between the disposable tip (104) and the rigid tube (102). In some embodiments, the rigid tube (102) may be defined with a bulge and the disposable tip (104) may be defined with a matching slit for placing the disposable tip (104) on the rigid tube (102) while still enabling free rotation of the disposable tip (104) relative to the rigid tube (102).

Figure 6:
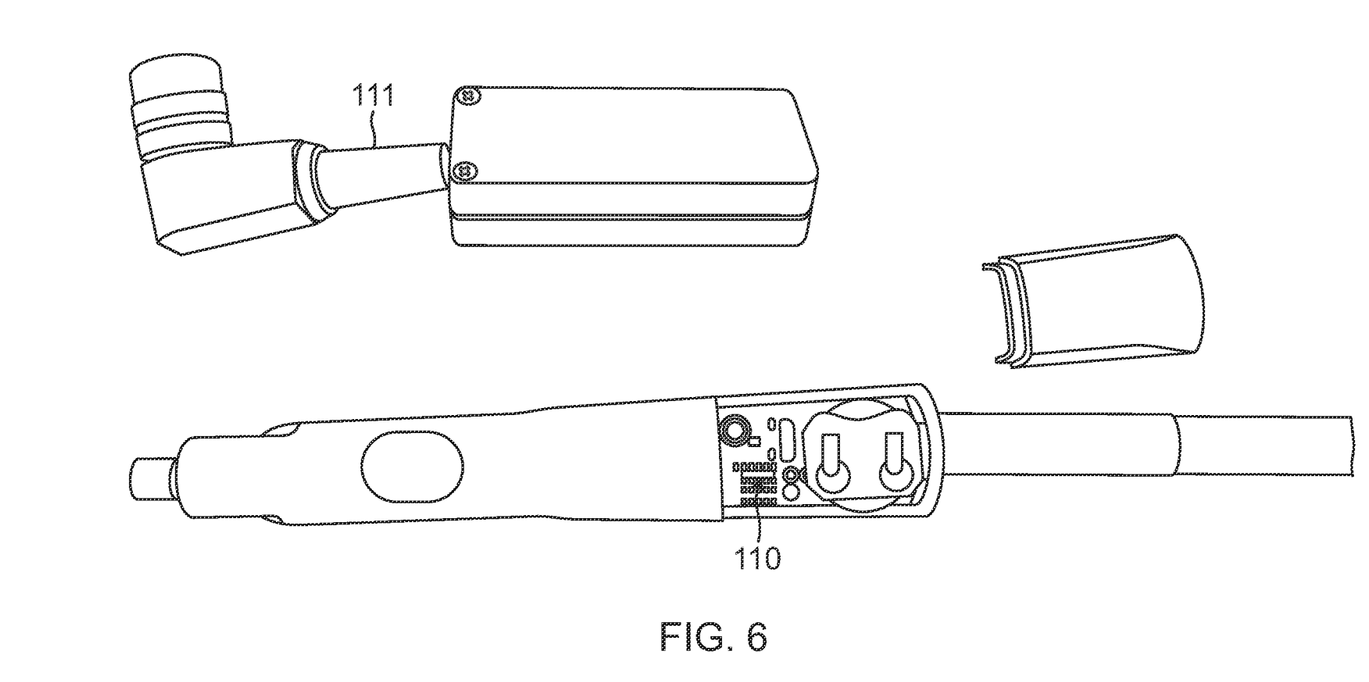
FIG. 6 shows a schematic view of the device of FIG. 1 with electronic components for electrical connection with a console, in accordance with some embodiments of the present disclosure.

FIG. 6 shows a top view of the device (100). The cover member (103) may be configured to house a plurality of electronic components (110) such as but not limited to processor chips, radio-frequency identification (RFID) and one or more batteries. These components may allow the device to make a wired or wireless connection with an external console. The wired/wireless connection may help in tasks such as but not limited to transferring data etc. The electronic components within the device (100) may include a Bluetooth or WIFI or other components. This is important when there is no electrical wired connection between the device (100) and the console, since the flexible member (108) contains only the optical fiber and, as such, the on/off switch (109) needs to be connected to a device that, when pressed or moved, will cause the IPL or other light source to be activated. On the console, a so-called dongle (111), shown in FIG. 6, may be enabled to intercept the over-the-air Bluetooth or other wireless signal and cause the firing of the IPL or other light source. In some embodiments, the wireless connection may utilize infra-red (IR) signal, in which case pressing the on/off switch (109) may emit IR beam from an IR LED located on the device. The IR signal (beam) is received by a corresponding sensor in the console or in the room where the console is placed. The IR signal may also be transferred to the console through one or more fibers inside the fiber bundle (101). The wireless functionality may be energized by a regular battery, a rechargeable battery, a dedicated charging base, and/or a solar/photovoltaic cell, etc. In some embodiment, the fiber bundle (101), shown in FIG. 1, may have electrical wires configured to establish electrical connection between the device (100) and the console.

Figure 7A:
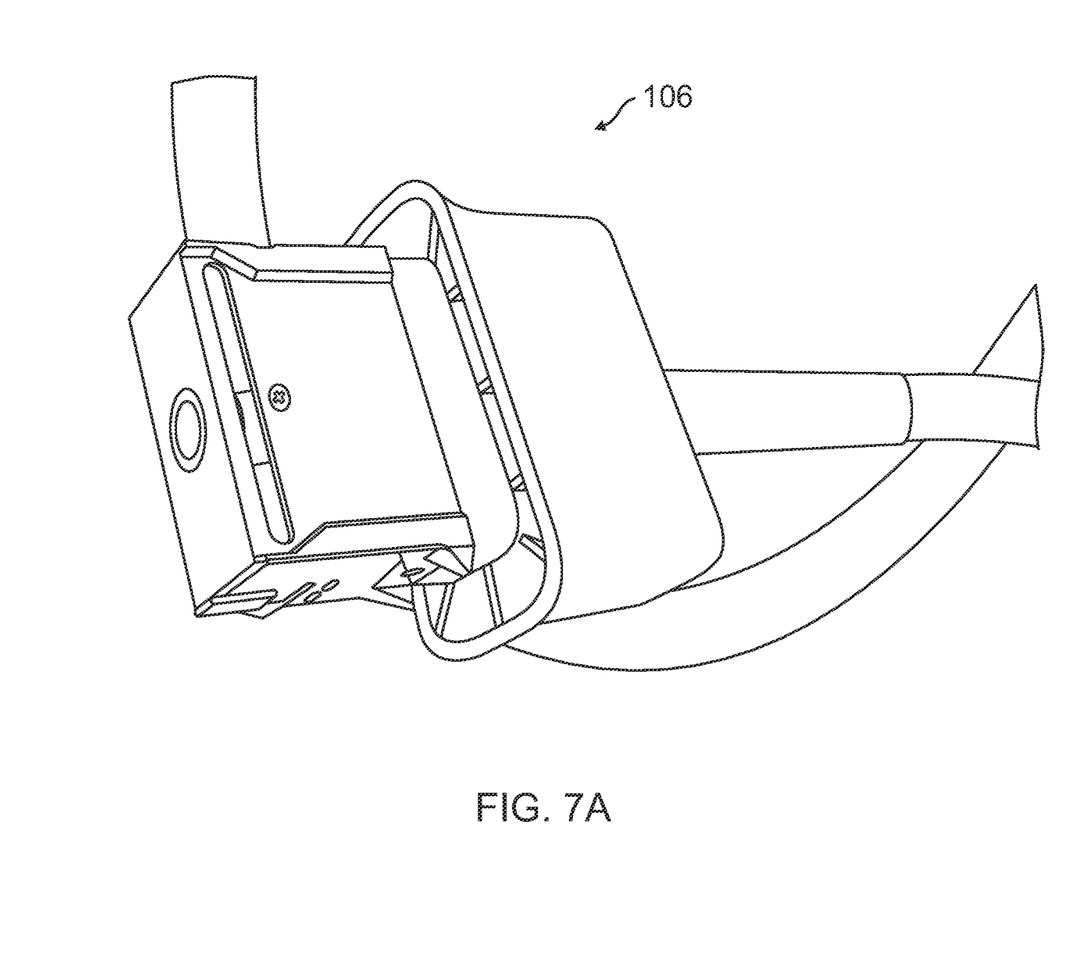
FIGS. 7A and 7B show perspective views of a connector of the device of FIG. 1 connectable with the console, in accordance with some embodiments of the present disclosure.
Figure 7B:
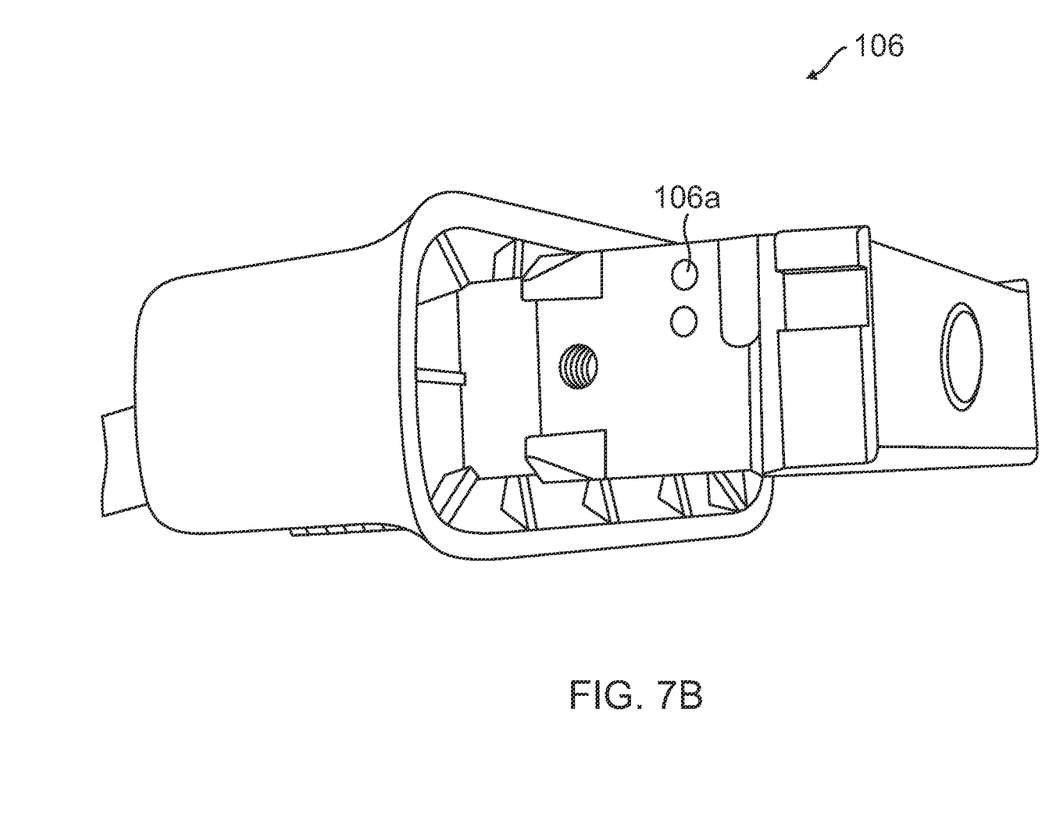

FIGS. 7A and 7B show the connector (106) that may be provided at the proximal end (101b) of the fiber bundle (101). In some embodiments, the connector (106) may be inserted or plugged into a cavity (107a) of an IPL handpiece device (107). However, the connector (106) may also be directly inserted into a cavity defined in the console (not shown in the figure) and the same should not be construed as a limitation of the present disclosure. The connector (106), as shown in FIG. 7B may have magnets (106a) that are intended to stimulate Reed Switches inside the IPL handpiece device (107). In another example, the connector (106) may include contact pins or RFID mechanism that are inserted with the connector (106) into the cavity of the IPL device or the console. The contact pins/RFID are provided to identify the insertion of the device (100) into the IPL device (107), so that activation of light energy and its extent through the fiber bundle (101) may be initiated.

In some embodiments of the present disclosure, the rotation of the disposable tip (104) along with the cover member (103) about the longitudinal axis (A-A) of the rigid tube (102) allows operation of the device in various orientations, thus assisting the operator to achieve required contact with the eyelid through the contact surface (104a) of the disposable tip (104) as may be required during the treatment.

In some embodiments of the present disclosure, the device (100) is easy to use, ergonomic for handling and is lightweight.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and are generally intended as "open" terms, e.g. the terms "including" and "includes" should be interpreted as "including/includes but not limited to," the term "having" should be interpreted as "having at least,", etc. It will be further understood by those within the art that, as an aid to understanding, the detailed description may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an", e.g., "a" and/or "an" should typically be interpreted to mean "at least one" or "one or more"; the same holds true for the use of definite articles used to introduce claim recitations. In addition, even if a specific number of an introduced claim recitation is explicitly recited, those skilled in the art will recognize that such recitation should typically be interpreted to mean at least the recited number, e.g., the bare recitation of "two recitations," without other modifiers, typically means at least two recitations, or two or more recitations.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following detailed description.

REFERRAL NUMERALS

| Referral numerals | Description |
| --- | --- |
| 100 | Device for treating eyelids |
| 101 | Fiber bundle |
| 101a | Distal end of the fiber bundle |
| 101b | Proximal end of the fiber bundle |
| 102 | Rigid tube |
| 102a | Slit |
| 103 | Cover member |
| 103a | Projection of the cover member |
| 104 | Disposable tip |
| 104a | Contact surface |
| 104b | Bulge |
| 104c | Notches |
| 105 | Bearing |
| 106 | Connector |
| 106a | Contact pin |
| 107 | IPL device |
| 107a | Cavity |
| 108 | Flexible member |
| 109 | Switch |
| 110 | Electronic components |
| 111 | Dongle |

The invention claimed is:

1. A device (100) for treating eyelids of a subject, the device (100) comprising:
a fiber bundle (101), having a distal end (101a) and a proximal end (101b), wherein the proximal end (101b) is connectable to an optical coupler designed for optical coupling with a light source and a portion of the fiber bundle (101) is housed by a flexible member (108) at the proximal end (101b);
a rigid tube (102) housing at least a portion of the distal end (101a) of the fiber bundle (101); and
a cover member (103) mounted around a portion of the rigid tube (102), wherein, the cover member (103) is rotatable relative to the rigid tube (102) during treatment of the eyelids of the subject with light from the light source.

2. The device (100) as claimed in claim 1, comprising a disposable tip (104) receivable by a free end of the rigid tube (102) and removably coupled to the cover member (103), wherein the disposable tip (104) includes a contact surface (104a) to contact the eyelids of the subject.

3. The device (100) as claimed in claim 2, wherein the disposable tip (104) is fixedly connected to the cover member (103), and both the disposable tip and the cover member are configured to be rotatable together relative to the rigid tube (102).

4. The device (100) as claimed in claim 2, wherein the contact surface (104a) of the disposable tip (104) is made of a bio-compatible material.

5. The device (100) as claimed in claim 1, wherein the cover member (103) is made of a polymeric material.

6. The device (100) as claimed in claim 1, wherein the rigid tube (102) is made of a metallic member.

7. The device (100) as claimed in claim 1, comprising at least one bearing (105) mounted between the rigid tube (102) and the cover member (103) to allow relative rotation of the cover member (103) with respect to the rigid tube (102).

8. The device (100) as claimed in claim 1, wherein the cover member (103) is configured to rotate about a longitudinal axis (A-A) of the rigid tube (102).

9. The device (100) as claimed in claim 1, wherein the proximal end (101b) of the fiber bundle (101) includes a connector (106) structured to be connectable to the optical coupler.

10. The device (100) as claimed in claim 1, wherein the light source comprises a cavity (107a), the cavity (107a) forming the optical coupler to accommodate the connector (106).

11. The device (100) as claimed in claim 9, wherein the connector (106) is defined with at least one contact pin (106a) to sense and identify insertion of the device (100) into the light source.

12. The device (100) as claimed in claim 1, wherein the rigid tube (102) is defined with a slit (102a) to accommodate a bulge (104b) of the disposable tip (104) and allow rotation of the disposable tip (104) relative to the rigid tube (102).

13. The device (100) as claimed in claim 2, wherein the cover member (103) includes a projection (103a), and the disposable tip (104) is defined with a plurality of notches (104c) to facilitate assembly of the cover member (103) with the disposable tip (104) through at least one notch of the plurality of notches (104c).

14. A system for performing treatment of eyelids of a subject, the system comprising:
a console configured to receive a light source, wherein the console is defined with a cavity to allow connection of a device, the device comprising:
a fiber bundle (101), having a distal end (101a) and a proximal end (101b), wherein the proximal end (101b) is connectable to an optical coupler designed for optical coupling with the light source;
a rigid tube (102) housing at least a portion of the distal end (101a) of the fiber bundle (101); and
a cover member (103) mounted around a portion of the rigid tube (102), wherein, the cover member (103) is rotatable relative to the rigid tube (102) during treatment of the eyelids of the subject;
a disposable tip (104) receivable by a free end of the rigid tube (102) and removably coupled to the cover member (103), the disposable tip (104) includes a contact surface (104a) to contact the eyelids of the subject.

15. The system as claimed in claim 14, wherein the console is configured to accommodate an IPL device (107).

16. The system as claimed in claim 15, wherein the IPL device (107) is defined with a cavity (107a) to accommodate the device (100).

17. A device (100) for treating eyelids of a subject, the device (100) comprising:
a fiber bundle (101), having a distal end (101a) and a proximal end (101b), wherein the proximal end (101b) is connectable to an optical coupler designed for optical coupling with a light source;
a rigid tube (102) housing at least a portion of the distal end (101a) of the fiber bundle (101); and
a cover member (103) mounted around a portion of the rigid tube (102), at least one bearing (105) mounted between the rigid tube (102) and the cover member (103) wherein, the cover member (103) is rotatable relative to the rigid tube (102) during treatment of the eyelids of the subject with light from the light source.

* * * * *